United States Patent
Ogawa et al.

(10) Patent No.: US 11,097,209 B2
(45) Date of Patent: Aug. 24, 2021

(54) SEPARATION METHOD, AND PRODUCTION METHOD FOR (METH)ACRYLATE

(71) Applicant: Mitsubishi Chemical Corporation, Chiyoda-ku (JP)

(72) Inventors: Yasushi Ogawa, Tokyo (JP); Masakazu Katou, Tokyo (JP); Yukihiro Hasegawa, Mie (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/820,933

(22) Filed: Mar. 17, 2020

(65) Prior Publication Data

US 2020/0215458 A1 Jul. 9, 2020

Related U.S. Application Data

(63) Continuation of application No. PCT/JP2018/036064, filed on Sep. 27, 2018.

(30) Foreign Application Priority Data

Sep. 29, 2017 (JP) .............................. JP2017-191140
Sep. 25, 2018 (JP) .............................. JP2018-178727

(51) Int. Cl.
*B01D 17/02* (2006.01)
*C07C 67/58* (2006.01)
(Continued)

(52) U.S. Cl.
CPC ......... *B01D 17/0208* (2013.01); *B01D 17/12* (2013.01); *C07C 67/08* (2013.01); *C07C 67/58* (2013.01); *C07C 69/54* (2013.01)

(58) Field of Classification Search
CPC ........ B01D 17/00; B01D 17/02; B01D 17/12; B01D 17/0208; C07C 67/58; C07C 69/54
See application file for complete search history.

(56) References Cited

U.S. PATENT DOCUMENTS 4,316,805 A * 2/1982 Faust ................. B01D 17/0202
                                                210/693
4,664,802 A * 5/1987 Lee ........................ B01D 17/00
                                                210/522
(Continued)

FOREIGN PATENT DOCUMENTS

CN          1318425 A          10/2001
CN          1343133 A           4/2002
(Continued)

OTHER PUBLICATIONS

Extended European Search Report dated Oct. 14, 2020 in corresponding European Patent Application No. 18861524.9, 10 pages.
(Continued)

*Primary Examiner* — Yate' K Cutliff
(74) *Attorney, Agent, or Firm* — Oblon, McClelland, Maier & Neustadt, L.L.P.

(57) ABSTRACT

An object of the present invention is to provide a separation method capable of efficiently separating a light liquid and a heavy liquid from a mixed liquid containing the light liquid, the heavy liquid, and an emulsion liquid of the light liquid and the heavy liquid, such as an emulsion-layer extraction liquid in a vicinity of an interface in an extraction column. The present invention relates to a separation method for continuously separating a light liquid and a heavy liquid having a specific gravity larger than that of the light liquid from a mixed liquid containing the light liquid, the heavy liquid, and an emulsion liquid of the light liquid and the heavy liquid by introducing the mixed liquid into a separation tank, in which a specific separation layer is used for the separation tank.

9 Claims, 3 Drawing Sheets

(51) Int. Cl.
  *B01D 17/12* (2006.01)
  *C07C 69/54* (2006.01)
  *C07C 67/08* (2006.01)

(56) References Cited

U.S. PATENT DOCUMENTS

| 6,537,458 | B1 | 3/2003 | Polderman |
| 2003/0127376 | A1 | 7/2003 | Maddock et al. |
| 2004/0260122 | A1 | 12/2004 | Yada et al. |
| 2007/0021633 | A1 | 1/2007 | Yada et al. |
| 2007/0256921 | A1 | 11/2007 | Yada et al. |

FOREIGN PATENT DOCUMENTS

| CN | 1564798 A | 1/2005 |
| CN | 203108274 U | 8/2013 |
| FR | 3 002 743 A1 | 9/2014 |
| FR | 3 037 049 A1 | 12/2016 |
| JP | 61-067812 U | 5/1986 |
| JP | 06-045602 U | 6/1994 |
| JP | 2003-226672 A | 8/2003 |
| JP | 2005-145880 A | 6/2005 |
| JP | 2014-162764 A | 9/2014 |
| JP | 2014-162765 A | 9/2014 |
| RU | 2 372 130 C9 | 10/2010 |

OTHER PUBLICATIONS

Indian Office Action dated Jan. 29, 2021 in Indian Patent Application No. 202017012916 (with English translation), 6 pages.
Russian Federation Search Report dated Feb. 26, 2021 in Russian Federation Patent Application No. 2020111570 (with English translation), 4 pages.
International Search Report dated Dec. 25, 2018 in PCT/JP2018/036064 filed on Sep. 27, 2018 (with English Translation), 5 pages.
Office Action dated May 21, 2021, in corresponding Chinese Patent Application No. 201880061109.2, (with English translation).
Rongjun MA, "Extractive Metallurgy", Beijing, Matallurgical Industry Press p. 303 (Aug. 31, 2009). (with Partial English translation).

* cited by examiner

SEPARATION METHOD, AND PRODUCTION METHOD FOR (METH)ACRYLATE

TECHNICAL FIELD

The present invention relates to a separation method for efficiently separating a mixed liquid containing a light liquid, a heavy liquid having a specific gravity larger than that of the light liquid, and an emulsion liquid of the light liquid and the heavy liquid. The present invention also relates to a production method for (meth)acrylate using the separation method.

BACKGROUND ART

Liquid-liquid extraction is a method to recover or remove valuables or impurities contained in a certain solution a, in which a solution b, which forms two liquid layers with the solution a, is used to contact the solution a in a liquid state, and the valuables or impurities in the solution a moves to the solution b. Liquid-liquid extraction is a purification method widely used as well as distillation in a production process of chemical products.

A common apparatus used for the liquid-liquid extraction is an extraction column. In the extraction column, a solution (heavy liquid) having a relatively large specific gravity is supplied from an upper part of the column, and a solution (light liquid) having a relatively small specific gravity is supplied from a lower part of the column. In the extraction column, valuable collection or impurity removal is performed in a step in which the heavy liquid descending in the extraction column is in a counterflow contact with the light liquid rising in the extraction column. Most commonly, the light liquid mainly contains a hydrophobic organic substance, and the heavy liquid mainly contains water.

In the counterflow contact step, when liquid droplets of the heavy liquid descend in the light liquid, in other words, when the heavy liquid is a dispersed phase and the light liquid is a continuous phase, an interface, which is a boundary region between a light-liquid layer and a heavy-liquid layer, is formed in the lower part of the extraction column. In contrast, when the light liquid is a dispersed phase and the heavy liquid is a continuous phase, an interface between the light-liquid layer and the heavy-liquid layer is formed on the upper part of the extraction column. In the case of an extraction column which continuously performs an extraction operation, control of the interface is essential for stable operation.

When a component having a surface active action is contained in a handling fluid of the extraction column, emulsification which is a state where fine droplets of one of the heavy liquid and light liquid are dispersed in the other one thereof is likely to occur. A specific gravity of the emulsified liquid is between that of the light liquid and that of the heavy liquid, so that the emulsified liquid is not discharged from the top or bottom of the extraction column, but accumulates in a vicinity of the interface to form an emulsion layer. It is difficult to detect the interface due to the emulsion layer, and in association with the accumulation of the emulsion liquid, adverse effects such as mixing of the emulsified liquid in a subsequent step are caused. Therefore, although various measures to prevent emulsification are taken, continuous or intermittent extraction of the emulsion layer is performed when the measures are insufficient.

In a step of producing (meth)acrylate by subjecting (meth) acrylic acid and alcohol to an esterification reaction, a trace amount of (meth)acrylic acid polymer, (meth)acrylate polymer, and a copolymer thereof are generated as by-products. These by-product polymers, particularly, copolymers having a hydrophilic (meth)acrylic acid group and a hydrophobic (meth)acrylate group exhibit a high surface active action, and thus formation of the emulsion layer in the extraction column is promoted.

As a method for removing such by-product polymers, for example, Patent Literature 1 discloses a method for removing by-products, such as neutralized salts, polymers and sludge, by extracting a part of a water layer and an organic layer in a vicinity of the interface when the (meth)acrylate-containing liquid, which is obtained by esterifying (meth) acrylic acid and alcohol in the presence of an acid catalyst, is washed and/or neutralized in an extraction column.

Patent Literature 2 discloses a method in which, in a production process for (meth)acrylate, an oil/water mixture in an interface inside a stationary tank is extracted and allowed to stand still for 2 hours or longer to allow water to be separated from oil, and then the oil layer is circulated in the production process.

CITATION LIST

Patent Literature

Patent Literature 1: JP-A-2003-226672
Patent Literature 2: JP-A-2014-162764

SUMMARY OF INVENTION

Technical Problem

Although extraction of an emulsion layer in a vicinity of an interface in an extraction column is important for stable operation of production equipment, the extraction of the emulsion layer causes a workload for an operator to no small extent. In general, an interface position in the extraction column is automatically calculated by measuring a differential pressure and buoyancy based on specific gravities of a heavy liquid and a light liquid and a specific gravity difference thereof. However, when the specific gravities of the heavy liquid and the light liquid vary, the calculated interface position has an error corresponding to a fluctuation range of the specific gravity.

There is also a method for directly measuring the interface position by radio waves or light. However, not only the formed emulsion layer interferes with the measurement, but also fouling due to polymers on an apparatus detection part occurs in the case of (meth)acrylate which is an easily polymerizable compound. Accordingly, it is difficult to obtain stable measurement results.

Therefore, there is a need for the operator to go directly to the production equipment and to work for extracting the emulsion layer with visually confirming the interface position. It was a workload for the operator that after allowing the extracted emulsion layer to stand still in the separation tank, a separation status of the light liquid layer and the heavy liquid layer was confirmed and one or both of the light liquid layer and the heavy liquid layer was/were circulated to the extraction column or other steps, and the remaining emulsion layer was disposed.

If not only the emulsion layer but also a part of the light liquid layer and the heavy liquid layer located above and below the emulsion layer are extracted together, an accurate interface position is not required. However, amount of liquids to be extracted increases, and thus the frequency of the operation of circulating the extracted liquid to another step increases. The work frequency can be reduced by increasing a size of the separation tank. However, an amount of circulating liquids for each work increases, and thus a work time itself does not change or becomes longer.

The present invention has been made in view of the above problems in the related art, and an object thereof is to provide a separation method capable of efficiently separating a light liquid and a heavy liquid from a mixed liquid containing the light liquid, the heavy liquid, and an emulsion liquid of the light liquid and the heavy liquid, such as an emulsion-layer extraction liquid in a vicinity of an interface in an extraction column.

Another object of the present invention is to provide a production method for (meth)acrylate using the separation method.

Solution to Problem

The present inventors have found that, as a result of investigations to solve the above problems, a workload of an operator can be greatly reduced by using a separation tank designed to separate the heavy liquid and the light liquid based on a difference in the specific gravities of the two liquids, and to automatically feed the heavy liquid and the light liquid to a target location.

The present invention has been accomplished based on such findings and is summarized as follows.

[1] A separation method, which is a method for continuously separating a light liquid and a heavy liquid having a specific gravity larger than that of the light liquid from a mixed liquid containing the light liquid, the heavy liquid, and an emulsion liquid of the light liquid and the heavy liquid by continuously introducing the mixed liquid into a separation tank,
wherein the separation tank contains:
a tank body;
a chamber A into which the mixed liquid is introduced and in which an interface between the light liquid and the heavy liquid is formed, a chamber B into which the light liquid flows from the chamber A by overflowing an overflow part, and a chamber C into which the heavy liquid flows from a bottom part of the chamber A via a liquid transfer pipe, which are chambers respectively formed by partitioning an inside of the tank body by an erected wall erected from a bottom surface of the tank body; and
an extraction part for an emulsion liquid configured to extract the emulsion liquid from the middle of the chamber A in a vertical direction,
in which one end of the liquid transfer pipe is opened in the chamber A, and the other end thereof is opened in the chamber C,
an upper end of an erected wall partitioning the chamber A and the chamber C is configured to be positioned higher than the overflow part, and
wherein when a height from the bottom part of the tank body to the overflow part is defined as $h_1$,
a height from the bottom part of the tank body to an opening of the liquid transfer pipe in the chamber C is defined as $h_2$,
a height from the bottom part of the tank body to the interface in the chamber A is defined as $h_1 \cdot \alpha$, and
a ratio $P_H/P_L$ of specific gravity $P_H$ of the heavy liquid to specific gravity $P_L$ of the light liquid is defined as X,
a relationship of $\alpha = (h_2 \times X - h_1)/h_1(X-1)$ is established,
$\alpha \geq 0.2$ when X is the minimum value $X_{min}$, and
$\alpha \geq 0.7$ when X is the maximum value $X_{max}$.

[2] The separation method according to [1], wherein the separation tank includes a detection part configured to confirm presence or absence of the emulsion liquid by detecting the height from the bottom part of the tank body to the interface in the chamber A.

[3] The separation method according to [2], wherein the detection part is a sight-through part for viewing the inside of the tank body, which is provided in the tank body.

[4] The separation method according to any one of [1] to [3], wherein the separation tank includes an illumination part configured to illuminate the inside of the tank body.

[5] The separation method according to any one of [1] to [4], wherein at least one of the chamber B and the chamber C of the separation tank is constituted of one chamber or a plurality of chambers,
when at least one of the chamber B and the chamber C of the separation tank is constituted of a plurality of chambers, the respective chambers are partitioned by an erected wall erected from the bottom surface of the tank body, and are connected in series by an overflow part or a connection pipe provided on the erected wall.

[6] The separation method according to any one of [1] to [5], wherein the tank body is a horizontal cylindrical container or a vertical cylindrical container.

[7] The separation method according to any one of [1] to [6], wherein the separation tank includes outflow parts configured to allow liquids to flow out from the chamber B and the chamber C respectively so as to keep liquid levels in the chambers within a predetermined range.

[8] The separation method according to any one of [1] to [7], wherein the separation tank includes at least one of a heat-retaining part configured to retain heat of the tank body and a heating part configured to heat the mixed liquid to be supplied to the tank body.

[9] The separation method according to any one of [1] to [8], wherein the mixed liquid contains a light liquid, a heavy liquid having a specific gravity larger than that of the light liquid, and an emulsion liquid of the light liquid and the heavy liquid, which are extracted from a vicinity of an interface in an extraction column.

[10] The separation method according to any one of [1] to [9], wherein the heavy liquid is introduced into the chamber A in advance of a start of operation of the separation tank.

[11] A production method for (meth)acrylate using the separation method according to any one of [1] to [10] in production of (meth)acrylate.

Effects of Invention

According to the separation method of the present invention, the light liquid and the heavy liquid can be efficiently separated from the mixed liquid containing the light liquid, the heavy liquid, and the emulsion liquid of the light liquid and the heavy liquid, and the light liquid and heavy liquid, which are separated, can be automatically fed to the target location. Therefore, when extraction of the emulsion layer deposited in the vicinity of the interface in the extraction column, separation of the light liquid and the heavy liquid accompanying the extraction, and circulation of the extracted liquid to the production process are performed, the workload of the operator can be reduced.

The separation method according to the present invention is applied to the production process for (meth)acrylate, whereby it is possible to perform the extraction of the liquids in a vicinity of the interface formed in the extraction column when (meth)acrylate-containing liquid, which is obtained by esterifying (meth)acrylic acid and alcohol in the presence of an acid catalyst, is washed and/or neutralized in an extraction column. In addition, a target (meth)acrylate layer and a water layer can be automatically separated from the extracted liquid and recovered separately, and a work efficiency and a production efficiency can be greatly improved.

DESCRIPTION OF EMBODIMENTS

Figure 1:
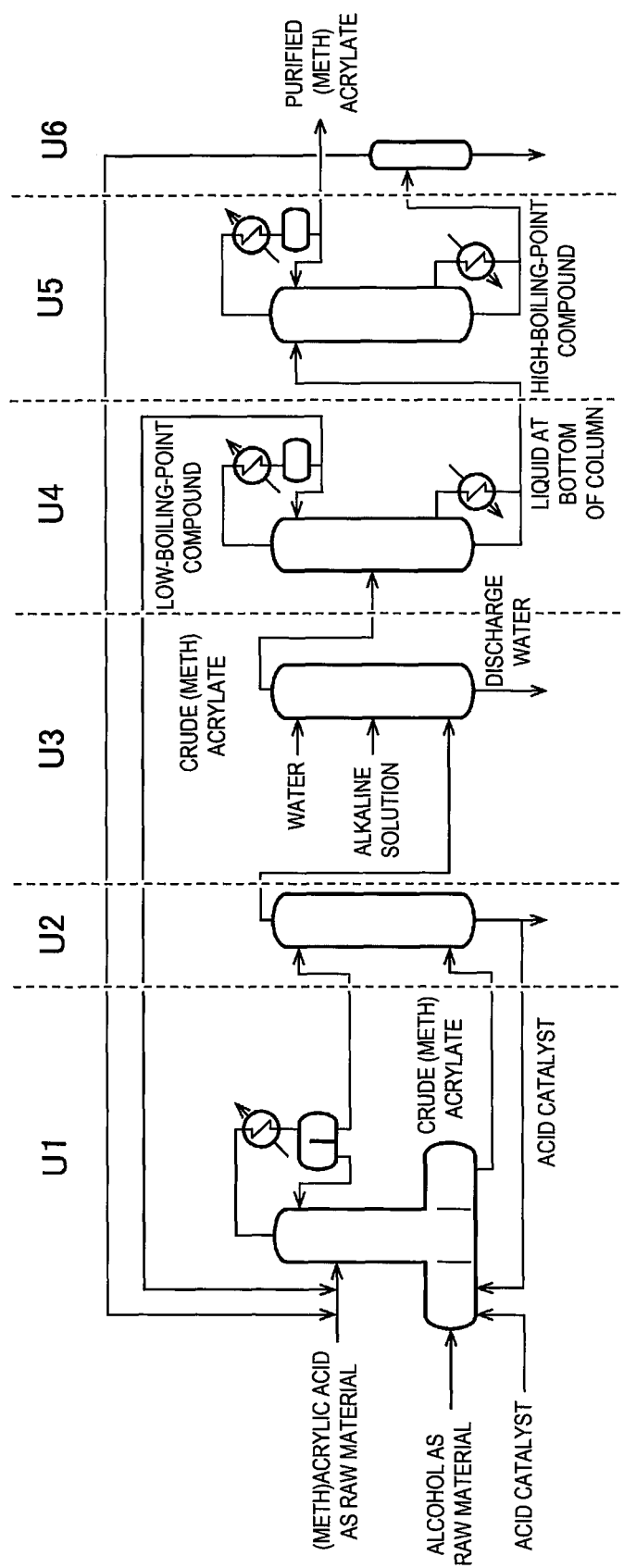
FIG. 1 is a schematic view showing a production process for (meth)acrylate.

Hereinafter, although the present invention will be described in detail with reference to the drawings, the present invention is not limited to the following description, and various modifications can be made within the scope of the present invention.

In the present invention, the term "vertical direction" means a direction of gravity (i.e., downward) and an opposite direction thereof (i.e., upward).

In the present invention, the term "bottom surface" means a surface located at the lowermost position in the vertical direction.

In the present invention, the term "(meth)acrylic" means acrylic or methacrylic.

A separation method according to the present invention is a method in which a mixed liquid containing a light liquid, a heavy liquid having a specific gravity larger than that of the light liquid, and an emulsion liquid of the light liquid and the heavy liquid is continuously introduced into a separation tank so as to continuously separate the light liquid and the heavy liquid from the mixed liquid. A separation tank according to the present invention described below is used as the separation tank.

Here, the sentence "a mixed liquid containing a light liquid, a heavy liquid having a specific gravity larger than that of the light liquid, and an emulsion liquid of the light liquid and the heavy liquid is continuously introduced into a separation tank" means a state where the mixed liquid is introduced into a chamber A described below without stopping for one hour or more even if there is a difference in the amount of the mixed liquid introduced per unit time.

In general, a flow rate of the mixed liquid introduced into the separation tank per unit time is 10 kg/hr or higher, preferably 20 kg/hr or higher, and more preferably 40 kg/hr or higher. The time for continuously introducing the mixed liquid into the separation tank according to the present invention at such introduction flow rate is at least 12 hours or longer, preferably 24 hours or longer, and more preferably 36 hours or longer.

Similarly, the phrase "so as to continuously separate the light liquid and the heavy liquid from the mixed liquid" means that the light liquid and the heavy liquid respectively flow from the chamber A described below into a chamber B and a chamber C in accordance with the introduction amount thereof, from a mixed liquid continuously introduced into the separation tank according to the present invention.

The emulsion liquid is required to be periodically extracted from the mixed liquid. The extraction of the emulsion liquid is preferably performed at a frequency lower than once every 6 hours, is more preferably performed at a frequency lower than once per day, and is particularly preferably performed at a frequency lower than once per week, from the viewpoint of reducing a workload.

The production method for (meth)acrylate according to the present invention is characterized by using the separation method according to the present invention, and other known steps, i.e., for example, steps shown in FIG. 1, can be used.

FIG. 1 is a schematic view showing a production process for (meth)acrylate, in which (meth)acrylic acid and alcohol are used as raw materials.

(Meth)acrylic acid as a raw material, alcohol as a raw material, and an acid catalyst are supplied to a reactive distillation part including a reactor and a distillation column, water as a reaction product is discharged from the top of the column, and crude (meth)acrylate is obtained from the reactor (reaction distillation step U1).

The acid catalyst contained in the crude (meth)acrylate is recovered by a solvent recovery part including an extraction apparatus, and is circulated to the reactive distillation part (solvent recovery step U2).

The crude (meth)acrylate from which the acid catalyst has been recovered is fed to a washing part including a neutralization washing column (an extraction column), and is washed with water or an alkaline solution as necessary (washing step U3).

A low-boiling-point compound such as alcohol in the washed crude (meth)acrylate is separated from the top of a distillation column in a low-boiling fraction separation part including the distillation column (low-boiling fraction separation step U4), and a liquid at the bottom of the distillation column is fed to a purification part including a distillation column (purification step U5).

A high-boiling-point compound is separated from a bottom of the distillation column of the purification part, and purified (meth)acrylate is obtained from a top of the distillation column.

The separated high-boiling-point compound is fed to a thermal decomposition part to decompose and recover valuables (thermal decomposition step U6).

Figure 2:
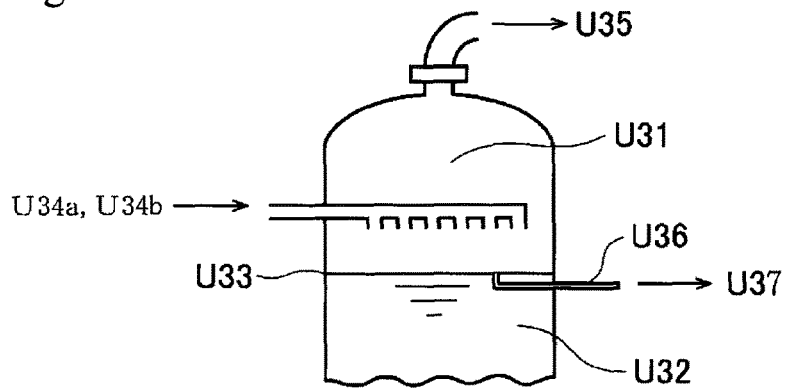
FIG. 2 is a schematic view showing an extraction part for an emulsion layer of a neutralization washing column (extraction column) provided in a washing part in FIG. 1.

FIG. 2 is a schematic view showing an extraction part for an emulsion layer of a neutralization washing column (an extraction column) provided in the washing part of FIG. 1, and shows an upper part of the neutralization washing column (the extraction column).

In the column upper part, a (meth)acrylate layer U31 and a water layer U32 are formed on an upper side and a lower side respectively with an interface U33 formed therebetween. U36 denotes a nozzle for extracting an emulsion layer U37 formed in a vicinity of the interface U33.

The crude (meth)acrylate from the solvent recovery part is introduced into the neutralization washing column from a lower part of the neutralization washing column, and is washed with the water U34$a$ or the alkaline aqueous solution U34$b$ as necessary, and then the washed crude (meth)

acrylate U35 is discharged from the upper part of the column and is transferred to the next low-boiling fraction separation part.

In the production process for such (meth)acrylate, the separation method according to the present invention is preferably used for continuously separating (meth)acrylate which is a light liquid and water which is a heavy liquid from an emulsion layer extracted from the neutralization washing column which is the extraction column, or the like, that is, from a mixed liquid containing (meth)acrylate which is a light liquid, water which is a heavy liquid, and an emulsified liquid of the light liquid and the heavy liquid.

Figure 3:
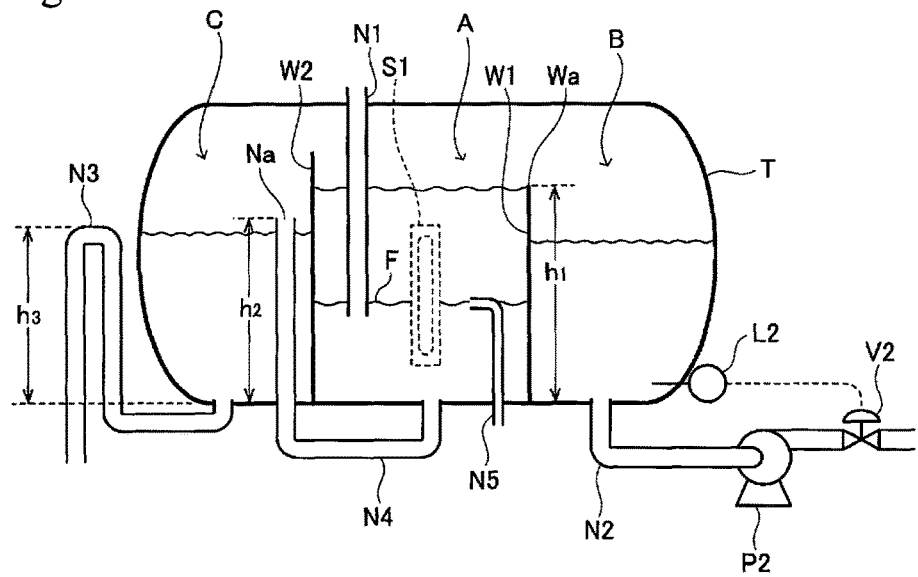
FIG. 3 is a schematic view showing an example of a separation tank used in the present invention.

FIG. 3 is a schematic view showing an example of a separation tank used in the separation method according to the present invention (hereinafter, referred to as "the separation tank according to the present invention").

A tank body T of the separation tank is partitioned by erected walls (partition walls) W1 and W2 erected from a bottom surface of the tank body T, so as to form chambers A to C. A mixed liquid containing a light liquid, a heavy liquid, and an emulsified liquid of the light liquid and the heavy liquid is continuously introduced into the chamber A from a supply pipe N1, and is separated, by being allowed to stand still in the chamber A, into the light liquid in an upper layer and the heavy liquid in a lower layer, and thus an interface between the light liquid and the heavy liquid is formed. In the production of (meth)acrylate, the mixed liquid corresponds to a mixed liquid of the emulsion layer extracted from the extraction column (e.g., the neutralization washing column in FIG. 2), the water layer, and the (meth)acrylate layer.

When a position, in a height direction, of a tip-end opening part of the supply pipe N1 for the mixed liquid is excessively low, the mixed liquid flowing from the supply pipe N1 may flow into the chamber C from a liquid transfer pipe N4 for the heavy liquid. In contrast, when the position in the height direction is excessively high, the mixed liquid may overflow an overflow part Wa and flow into the chamber B together with the light liquid flowing into the chamber B. Therefore, it is preferable that the tip-end opening part of the supply pipe N1 for the mixed liquid is located in a vicinity of the interface F formed in the chamber A.

In order to reduce convection of the liquids in the chamber A, it is preferable that the tip end part of the supply pipe N1, which extends downward from the upper part of the chamber A of the tank body T, is bent in a horizontal direction, or the opening part is expanded.

An upper end of the erected wall W1 serves as the overflow part Wa, and the light liquid in the chamber A overflows the overflow part Wa so as to flow into the chamber B which is adjacent to the chamber A via the erected wall W1. The height of the overflow part Wa is a height of $h_1$ from a bottom part of the tank body T.

A lower part of the chamber B is provided with an extraction pipe N2, which includes a liquid feed pump P2 and a flow-rate adjustment valve V2, and a liquid level gauge L2. An excess portion of the light liquid flowing into the chamber B can be automatically extracted so as to be fed to another step while the height of a liquid level in the chamber B is kept constant, by a control system (which is not shown in the Figure) which adjusts the flow-rate adjustment valve V2 in accordance with measurement values of the liquid level gauge L2.

A bottom part of the chamber A is provided with the liquid transfer pipe N4, and an tip end side of the liquid transfer pipe N4 opens toward a chamber C side. The heavy liquid in the chamber A flows into the chamber C, which is adjacent to the chamber A via the erected wall W2, through the liquid transfer pipe N4. The height of a tip-end opening Na of the liquid transfer pipe N4 is a height of $h_2$ from the bottom part of the tank body T. An excess portion of the heavy liquid flowing into the chamber C is automatically discharged by overflow while the height of a liquid level in the chamber C is kept constant by an extraction pipe N3 having a U-shape. The maximum height $h_3$ of the extraction pipe N3 serving as an overflow part is less than the height $h_2$ of the tip-end opening Na of the liquid transfer pipe N4 in the chamber C.

An upper end of the erected wall W2 partitioning the chamber A and the chamber C is positioned higher than the upper end of the erected wall W1 which is the overflow part Wa and partitions the chamber A and the chamber B. In FIG. 3, the upper end of the erected wall W2 is separated from the upper surface of the tank body T. However, as long as the upper end of the erected wall W2 is positioned higher than the upper end of the erected wall W1, the upper end of the erected wall W2 may contact an inner upper surface of the tank body T so as to be integrated with the tank body T. In addition, as for the erected wall W1, as long as an overflow part is formed, an opening serving as an overflow part may be provided thereon in a state where the upper end of the erected wall W1 itself contacts the inner upper surface of the tank body T.

The emulsion layer in the vicinity of the interface F formed in the middle part (intermediate part in the height direction) of the chamber A in the vertical direction is discharged by an emulsion-layer extraction pipe N5. That is, the amount of emulsion layer deposited at the intermediate part of the chamber A is increased while the mixed liquid is supplied through the supply pipe N1. Therefore, a sight glass S1 provided in the chamber A is confirmed and the emulsion layer is discharged using the emulsion-layer extraction pipe N5 as necessary in order to prevent the emulsion layer from flowing into the chamber B or chamber C.

In order to facilitate confirmation by the sight glass S1, it is preferable to separately provide a window for introducing a light source into the tank body T, as an illumination part. When the separation tank according to the present invention is applied to the production of (meth)acrylate, the window is preferably a structure capable of shielding light other than the period of confirmation work with the sight glass S1 since light promotes polymerization of (meth)acrylic acid or (meth)acrylate.

In FIG. 3, the sight glass S1, which is a sight-through part for viewing the inside of the tank body, is provided, as a detection part for confirming presence or absence of the emulsion liquid by detecting the height of the interface in the chamber A, on a wall surface of the chamber A of the tank body T. With regard to the sight glass, there is a case (direct type) where an opening part is provided directly on the tank body T and a glass window is provided on the opening part, and there is another case (indirect type) where a part of the liquid in the tank body T is extracted by a pipe and introduced into a transparent glass tube, and confirmation is performed by the glass tube. It is difficult to reproduce a position and the deposition amount of an emulsion layer, which are identical to those in the layer, in the glass tube, and thus the former one (direct type) is preferred.

As described above, when the mixed liquid is introduced into the chamber A, the emulsion layer accumulates around the interface F formed in the chamber A. The position of the interface F is determined by the height $h_1$ of the overflow part Wa, the height $h_2$ of the tip-end opening Na of the liquid transfer pipe N4, and the specific gravities of the heavy liquid and the light liquid.

When a ratio $P_H/P_L$ of a specific gravity $P_H$ of the heavy liquid to a specific gravity $P_L$ of the light liquid is defined as X and the height to the interface F formed in the chamber A is defined as $h_1 \cdot \alpha$, a relationship of $\alpha=(h_2 \times X-h_1)/h_1(X-1)$ is established.

The height $h_1 \cdot \alpha$ of the interface formed in the chamber A is preferably the height of the middle part of the chamber A in the height direction (i.e., $\alpha \approx 0.5$), from the viewpoint of preventing the emulsion layer accumulated in the chamber A from flowing into the chamber B or the chamber C and reducing the frequency of extraction work of the emulsion layer from the chamber A. However, the ratio X varies depending on the type of the mixed liquid to which the separation tank is applied. In addition, even if the mixed liquids are the same, a composition of both the heavy liquid and the light liquid varies in accordance with changes of operation conditions and the like. Therefore, the ratio X is not a constant value, and varies in a constant range (the minimum value $X_{min}$ to the maximum value $X_{max}$).

Therefore, it is required to always form the interface F in the chamber A within the variation range of the ratio X, and $\alpha$ is preferably from 0.2 to 0.7, and more preferably from 0.25 to 0.6 from the viewpoint of preventing the emulsion layer from flowing into the adjacent chamber with the accumulation of the emulsion layer.

When the average value of the minimum value $X_{min}$ and the maximum value $X_{max}$ is defined as $X_{ave}$, $X_{min}$ is preferably equal to or more than $X_{ave} \times 0.90$, and more preferably equal to or more than $X_{ave} \times 0.95$. Further, $X_{max}$ is preferably equal to or less than $X_{ave} \times 1.10$, and x more preferably equal to or less than $X_{ave} \times 1.05$.

Therefore, in the separation method according to the present invention, within an assumed specific gravity range of the light liquid and heavy liquid in the mixed liquid to be separated in the separation tank according to the present invention, when a height from the bottom part of the tank body T to the overflow part Wa is defined as $h_1$, a height from the bottom part of the tank body T to an tip-end opening part Na of the liquid transfer pipe N4 is defined as $h_2$, a height from the bottom part of the tank body T to the interface F in the chamber A is defined as $h_1 \cdot \alpha$, and the minimum value and the maximum value of the ratio $P_H/P_L$ of the specific gravity $P_H$ of the heavy liquid to the specific gravity $P_L$ of the light liquid are respectively defined as $X_{min}$ and $X_{max}$, design is decided so that the relationships of $\alpha=(h_2 \times X_{min}-h_1)/h_1(X_{min}-1) \geq 0.2$ when the ratio $X=X_{min}$, and $\alpha=(h_2 \times X_{max}-h_1)/h_1(X_{max}-1) \leq 0.7$ when the ratio $X=X_{max}$, arc established.

More preferably, the established relationships are $\alpha=(h_2 \times X_{min}-h_1)/h_1(X_{min}-1) \geq 0.25$ when the ratio $X=X_{min}$, and $\alpha=(h_2 \times X_{max}-h_1)/h_1(X_{max}-1) \leq 0.6$ when the ratio $X=X_{max}$.

Namely, the separation method according to the present invention is characterized in that when a separation tank which includes:

a tank body;

a chamber A into which the mixed liquid is introduced and in which an interface between the light liquid and the heavy liquid is formed, a chamber B into which the light liquid flows from the chamber A by overflowing an overflow part, and a chamber C into which the heavy liquid flows from a bottom part of the chamber A via a liquid transfer pipe, which are chambers respectively formed by partitioning an inside of the tank body by an erected wall erected from a bottom surface of the tank body; and an extraction part for an emulsion liquid configured to extract the emulsion liquid from the middle of the chamber A in a vertical direction, in which one end of the liquid transfer pipe communicates with the chamber A, and the other end thereof is opened in the chamber C, and an upper end of an erected wall partitioning the chamber A and the chamber C is configured to be positioned higher than the overflow part, is used to continuously perform separation of the mixed liquid, the height $h_1$ of the overflow part and the height $h_2$ of the tip-end opening part Na of the liquid transfer pipe N4 are designed to an appropriate height so that a falls within the appropriate range as described above even if the specific gravities of the light liquid and the heavy liquid may vary.

Therefore, for example, a plurality of liquid transfer pipes N4 having different heights $h_2$ may be provided in the chamber C, and the nozzles to be used may be switched and used according to the conditions. In this way, an application range of the operation conditions can be widened by designing the height $h_2$ and the height $h_1$ to be variable.

In the present invention, the term "bottom part of the tank body" when measuring the height $h_1$ and the height $h_2$ refers to a location in the opening surface of the liquid transfer pipe N4 on the chamber A side, which is closest to the interface between the light liquid and the heavy liquid.

Figure 4:
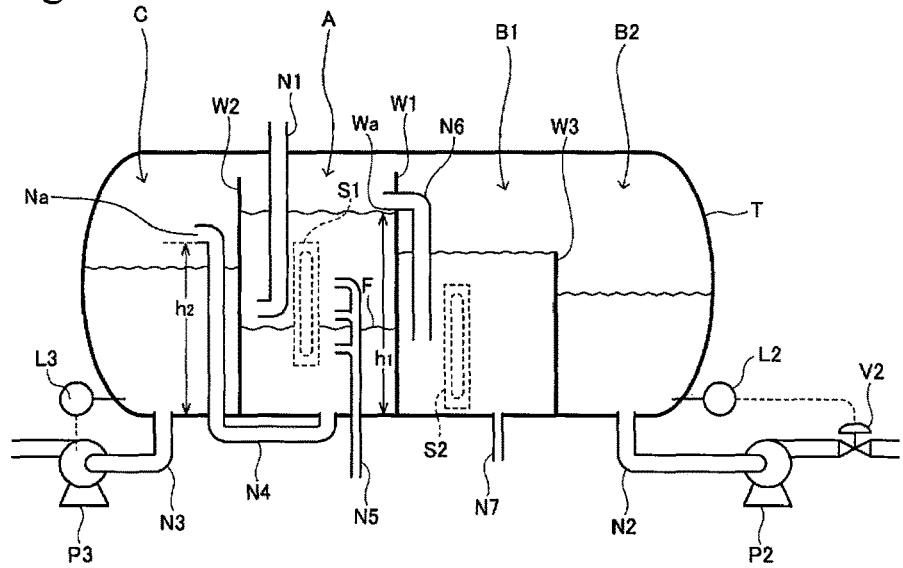
FIG. 4 is a schematic view showing a different example of the separation tank used in the present invention.

The term "overflow part" at measuring the height $h_1$ refers to an upper end when the upper end of the erected wall W1 serves as an overflow part as shown in FIG. 3. In addition, when a lower opening part of the connection pipe N6 on the base end side (chamber A side) is an overflow part as shown in FIG. 4, the term "overflow part" at measuring the height $h_1$ refers to a location in the opening surface, which is closest to the interface between the light liquid and the heavy liquid.

The term "tip-end opening" when measuring the height $h_2$ refers to a location of the opening surface, which is closest to the interface between the light liquid and the heavy liquid.

Figure 6:
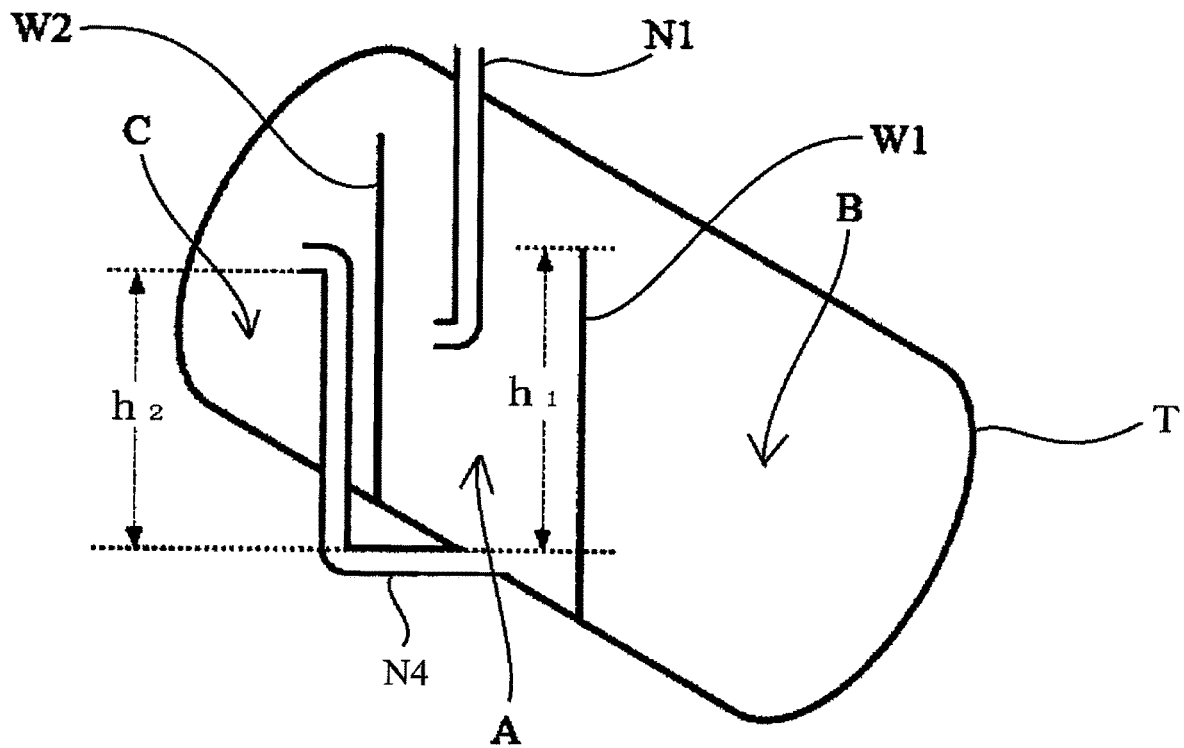
FIG. 6 is a schematic view showing an example of a tank body, which shows a height of each part in a case where a cylindrical container is inclined as a tank body provided in the separation tank used in the present invention.

For example, as shown in FIG. 6, when a cylindrical container is installed as the tank body T such that an axial direction thereof is not a horizontal direction but an inclined direction, the heights $h_1$ and $h_2$ of the respective parts are shown in FIG. 6. In FIG. 6, members having the same functions as those shown in FIG. 3 are denoted by the same symbols.

Since a decrease rate of the emulsion layer according to standing still in the chamber A is accelerated by an increase in the liquid temperature, the following items (1) and (2) and the like are preferably performed.

(1) A heating part such as a heat exchanger for heating the mixed liquid to be supplied to the separation tank is provided in front of the supply pipe N1.

(2) To avoid a decrease in the liquid temperature due to heat dissipation, a heat retaining part such as hot water heat tracing and a heat retaining material is disposed on an outer periphery of the separation tank.

However, excessive heating from the outer periphery of the tank body of the separation tank is not preferred since convection of liquids occurs and thus a separation of each layer by standing still is interfered when the temperature difference of the liquid temperatures based on the location in the separation tank occurs. When warming by external circulation of liquids in the tank is unavoidable, it is preferable to devise a solution so as to minimize the amount of the circulating liquid.

FIG. 4 is a schematic view showing another example of the separation tank according to the present invention, and members having the same function as those shown in FIG. 3 are denoted by the same symbols.

In the separation tank, the inside of the tank body T is partitioned into the chamber A, a chamber B1, a chamber B2, and the chamber C by erected walls W1, W3, and W2. That is, a chamber into which a light liquid flows is partitioned into the chamber B1 and the chamber B2. The connection pipe N6 is provided on the erected wall W1. The lower opening part of the connection pipe N6 on the base end side (chamber A side) serves as the overflow part Wa. The tip end side of the connection pipe N6 is opened in a liquid in the chamber B1. A height of the erected wall W3 is lower than a height of the erected wall W1.

In this way, the chamber B may be a single chamber, or may be constituted of two or more chambers. When the chamber B is constituted of a plurality of chambers, the respective chambers may be connected in series by an erected wall(s) having an overflow part or a connection pipe(s) provided on an erected wall. The same applies to the chamber C as well.

The chamber B1 performs separation and discharge of an emulsion liquid when a trace amount of the emulsion liquid flows from the chamber A through the connection pipe N6, and includes a sight glass S2 for confirming the presence of the emulsion liquid and an extraction pipe N7 for discharging the emulsion liquid.

Similarly to the separation tank of FIG. 3, an excess portion of the light liquid flowing into the chamber B2 by overflowing the erected wall W3 is fed to another step while the height of a liquid level in the chamber B2 is kept constant, by an extraction pipe N2, a liquid feed pump P2, a flow-rate adjustment valve V2, and a liquid level gauge L2.

On the other hand, the heavy liquid in the chamber C is automatically extracted from an extraction pipe N3 by repeating operation and stop of a liquid feed pump P3 so that a detection value in a liquid level gauge L3 falls within a constant range.

In the separation tank of FIG. 4, a tip end of an emulsion-layer extraction pipe N5 includes suction ports at a plurality of positions (three positions in FIG. 4) in the height direction so as to correspond to fluctuations in the height of the interface F in the chamber A.

The chambers B and C preferably include an outflow part allowing the liquid to flow out so as to keep the heights of the liquid levels in the chambers within a predetermined range. As in the chamber B of FIG. 3 and the chamber B2 of FIG. 4, the outflow part may include an extraction pipe, a pump, a flow-rate adjustment valve, a liquid level gauge, and a control system which adjusts the valve in accordance with the measurement values in the liquid level gauge. As in the chamber C of FIG. 4, the outflow part may include an extraction pipe, a pump, a liquid level gauge, and a control system which adjusts a driving of the pump in accordance with the measurement values in the liquid level gauge. In addition, as in the chamber C of FIG. 3, the outflow part may include an extraction pipe. The outflow part may be a combination of these apparatuses.

Figure 5A:
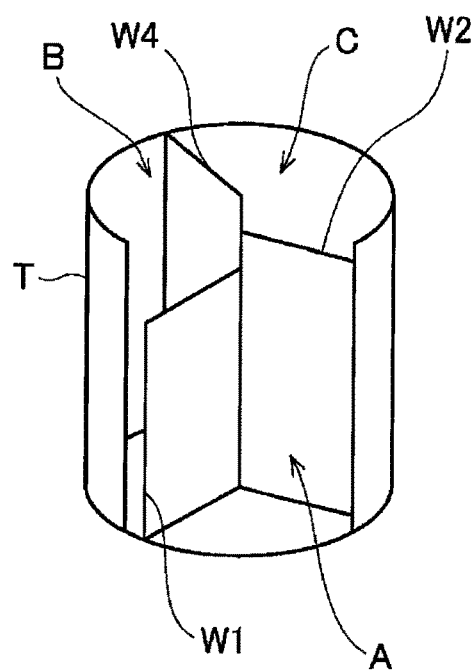
FIG. 5A and FIG. 5B are schematic views showing examples of a tank body provided in the separation tank used in the present invention.
Figure 5B:
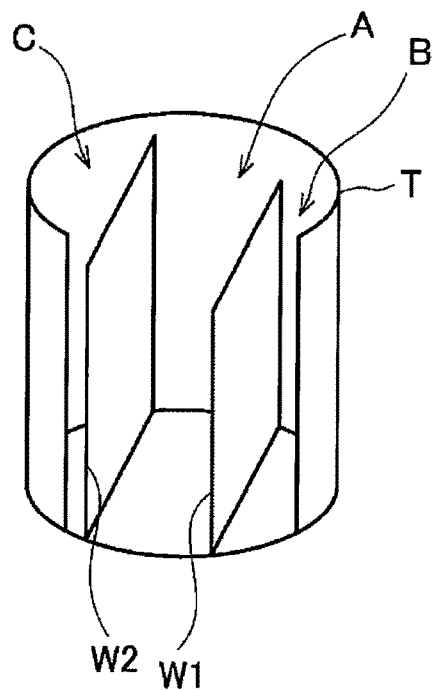

Although FIGS. 3 and 4 show the separation tank including the tank body T as a horizontal cylindrical container, the tank body T may be a vertical cylindrical container as shown in FIGS. 5A and 5B.

In the separation tank of FIG. 5A, chambers A, B, and C are formed in a partition manner by providing erected walls W1, W2, and W4 in the tank body T in a radial direction. In the separation tank of FIG. 5B, chambers A, B, and C are formed in a partition manner by providing erected walls W1 and W2 in parallel in the tank body T.

Considering a burden on the manufacturing of providing a plurality of erected walls (partition walls) in the tank body, easiness of entering a tank to work for maintenance when operation is stopped, or the like, the horizontal cylindrical container is better. However, since the vertical cylindrical container can allow a depth of a liquid in the tank to be deepened, the vertical cylindrical container is particularly preferred when the specific gravity difference between the heavy liquid and the light liquid is small, or when the specific gravity of each liquid varies greatly.

When a light liquid and a heavy liquid are separated, by using the separation tank according to the present invention, from a mixed liquid containing the light liquid, the heavy liquid, and an emulsion liquid of the light liquid and the liquid in accordance with the separation method according to the present invention, it is preferable that the heavy liquid is introduced into the chamber A of the separation tank in advance. The light liquid or the emulsion liquid can be prevented from flowing into the chamber C through the liquid transfer pipe N4 by introducing the heavy liquid in the chamber A in advance.

Although the theoretical minimum amount of the heavy liquid introduced into the chamber A of the separation tank is the inner volume of the liquid transfer pipe N4, it is preferable that a heavy liquid in an amount at which the liquid level of the heavy liquid is above the bottom of the sight glass is introduced. When the amount of the heavy liquid introduced into the chamber A is excessively large, the heavy liquid may flow into the chamber B from the chamber A by overflowing the overflow part Wa immediately after starting of an operation of the separation tank and introducing the mixed liquid into the chamber A from the supply pipe N1. Therefore, the amount of the heavy liquid introduced into the chamber A is an amount at which a height of a liquid level of the heavy liquid from the bottom surface of the tank body T is 0.2 to 0.7 times the height $h_1$ of the overflow part Wa, or is a height wherein a tip end of the supply pipe N1 is referred to as a rough guide.

A mixed liquid flowing from the supply pipe N1 is required to standing still in the chamber A for a predetermined time and be separated into a heavy liquid and a light liquid, so that it is required to design the separation tank according to the present invention such that a flow rate of the mixed liquid introduced from the supply pipe N1 is not excessively large relative to the capacity of the chamber A. Although a time required for separation of an emulsion layer varies greatly depending on properties of the emulsion layer, an average retention time of the supply liquid in the chamber A is preferably from 0.5 to 50 hours.

EXAMPLES

Hereinafter, the present invention will be described in more detail with Reference Example and Example.

Reference Example 1

In a commercial equipment shown in FIG. 1 for producing 70,000 tons of butyl acrylate per year, liquids in a vicinity of an interface in an extraction column of a washing part were continuously extracted at 60 kg/hr and supplied to a tank container. Supply of the liquids in the vicinity of the interface in the extraction column was continued for about 24 hours, and then a supply destination was changed to another tank container. In the tank container in which the supply was stopped, after allowing the liquids to stand still for 6 hours, a water layer and an emulsion layer were extracted from the lower part of the tank container sequentially with confirming liquid properties, and then a remaining acrylate layer was circulated to a supply solution line of the washing part. The same work was continued for each day during the operation of the equipment. Proportions of the water layer or the emulsion layer, and the acrylate layer formed for each work were not the same, and an automation in which a flow rate of an extraction liquid from the tank container is defined as a constant value could not be implemented.

Example 1

A commercial equipment shown in FIG. 1 for producing 80,000 tons of butyl acrylate per year was provided with a separation tank shown in FIG. 4, liquids in a vicinity of an interface in an extraction column of a washing part were continuously extracted at 100 kg/hr and continuously supplied to a chamber A of the separation tank. A supply amount was equivalent to an amount at which an average retention time in the chamber A was about 12 hours.

Prior to start of the operation of the separation tank, water was introduced into the chamber A of the separation tank in advance to reach a height of about 500 mm from the bottom part of the tank body T. A flow path of an extraction pipe was set so that a butyl acrylate layer separated in the chamber A and flowed from the chamber A to a chamber B was automatically circulated to a supply liquid line of the washing part. In addition, the flow path of the extraction pipe was set so a water layer separated in the chamber A and flowed into a chamber C was automatically supplied to a wastewater tank.

A fluctuation range $X_{min}$ to $X_{max}$ of an assumed ratio of a specific gravity $P_H$ of a heavy liquid to a specific gravity $P_L$ of a light liquid was 1.17 to 1.27. The separation tank was manufactured such that $h_1$=1,150 mm, $h_2$=1025 mm, and a height of an opening of a supply pipe N1 for a mixed liquid from the bottom part of the tank body T was 520 mm. A calculated value of α was 0.25 to 0.49.

During operation period of two weeks, field work was not required except that an emulsion layer deposited at an interface in the chamber A was extracted from an emulsion-layer extraction pipe N5 every week, and a daily interface position and a daily lamination state of the emulsion layer were confirmed. In addition, there was no problem in the separation tank including the washing part.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2017-191140) filed on Sep. 29, 2017 and Japanese Patent Application (Patent Application No. 2018-178727) filed on Sep. 25, 2018, the contents of which are incorporated herein by reference.

REFERENCE SIGN LIST

U1 Reactive distillation step
U2 Solvent recovery step
U3 Washing step
U4 Low-boiling fraction separation step
U5 Purification step
U6 Thermal decomposition step
U31 (Meth)acrylate layer
U32 Water layer
U33 Interface
U36 Extraction nozzle
W1, W2, W3, W4 Erected wall
S1, S2 Sight glass
P2, P3 Feed pump
L2, L3 Liquid level gauge
V2 Flow-rate adjustment valve
A, B, C, B1, B2 Chamber

The invention claimed is:

1. A separation method, for continuously separating a light liquid and a heavy liquid having a specific gravity larger than that of the light liquid from a mixed liquid containing the light liquid, the heavy liquid, and an emulsion liquid of the light liquid and the heavy liquid by continuously introducing the mixed liquid into a separation tank,
wherein the separation tank comprises:
a tank body;
a chamber A into which the mixed liquid is introduced and in which an interface between the light liquid and the heavy liquid is formed, a chamber B separated from the chamber A by an overflow part, and a chamber C separated from the chamber A by an erected wall erected from a bottom surface of the tank body, wherein an upper end of the erected wall partitioning the chamber A and the chamber C is positioned higher than the overflow part;
a liquid transfer pipe having one end opened at a bottom part of the chamber A and having the other end opened in the chamber C; and
an extraction part for an emulsion liquid configured to extract the emulsion liquid from a middle of the chamber A, the middle of the chamber A being defined in a vertical direction,
wherein when a height from a bottom part of the tank body to the overflow part is defined as $h_1$,
a height from the bottom part of the tank body to an opening of the liquid transfer pipe in the chamber C is defined as $h_2$,
a height from the bottom part of the tank body to the interface in the chamber A is defined as $h_1 \cdot \alpha$, and
a ratio $P_H/P_L$ of specific gravity $P_H$ of the heavy liquid to specific gravity $P_L$ of the light liquid is defined as X,
a relationship of $\alpha=(h_2 \times X - h_1)/h_1(X-1)$ is established, where a is in a range of 0.2-0.7,
wherein the separation tank includes a detection part configured to confirm presence or absence of the emulsion liquid by detecting the height from the bottom part of the tank body to the interface in the chamber A,
wherein the separation tank includes outflow parts configured to allow liquids to flow out from the chamber B and the chamber C respectively so as to keep liquid levels in the chambers within a predetermined range, and
wherein the mixed liquid contains the light liquid, the heavy liquid having the specific gravity larger than that of the light liquid, and an emulsion liquid of the light liquid and the heavy liquid, which are extracted from a vicinity of an interface in an extraction column,
the separation method further comprising the steps of:
introducing the mixed liquid into the chamber A, which forms the interface between the light liquid and the heavy liquid, overflowing the light liquid into the chamber B by the overflow part, and flowing the heavy liquid from the bottom part of the chamber A into the chamber C via the liquid transfer pipe, detecting the height of the emulsion liquid in the chamber A by the detection part, and extracting the emulsion liquid from the middle of the chamber A by the extraction part.

2. The separation method according to claim 1, wherein the detection part is a sight-through part for viewing the inside of the tank body, which is provided in the tank body.

3. The separation method according to claim 1, wherein the separation tank includes an illumination part configured to illuminate the inside of the tank body.

4. The separation method according to claim 1, wherein at least one of the chamber B and the chamber C of the separation tank is constituted of one chamber or a plurality of chambers, when at least one of the chamber B and the chamber C of the separation tank is constituted of a plurality of chambers, the respective chambers are partitioned by an erected wall erected from the bottom surface of the tank body, and are connected in series by an overflow part or a connection pipe provided on the erected wall.

5. The separation method according to claim 1, wherein the tank body is a horizontal cylindrical container or a vertical cylindrical container.

6. The separation method according to claim 1, wherein the separation tank includes at least one of a heat-retaining part configured to retain heat of the tank body and a heating part configured to heat the mixed liquid to be supplied to the tank body.

7. The separation method according to claim 1, wherein the heavy liquid is introduced into the chamber A in advance of a start of operation of the separation tank.

8. The separation method according to claim 1, wherein the light liquid comprises (meth)acrylate, and the heavy liquid comprises water.

9. A production method for (meth)acrylate, comprising:

reacting (meth)acrylic acid, alcohol, and an acid catalyst in a reactive distillation part including a reactor and a distillation column to obtain a crude (meth)acrylate from the reactor;

recovering the acid catalyst contained in the crude (meth)acrylate, followed by circulating the recovered acid catalyst to the reactive distillation part;

washing the crude (meth)acrylate from which the acid catalyst has been recovered in a neutralization washing column to produce a washed crude (meth)acrylate and a mixed liquid comprising (meth)acrylate;

separating a low-boiling-point compound from the washed crude (meth)acrylate by a second distillation column to obtain a liquid at a bottom of the second distillation column;

purifying the liquid obtained from the bottom of the second distillation column to obtain purified (meth)acrylate, and separating the mixed liquid by the separation method according to claim 1 to obtain additional purified (meth)acrylate.

* * * * *